United States Patent
Belkin

Patent Number: 5,882,323
Date of Patent: Mar. 16, 1999

[54] POLYCENTRIC HINGED ULNAR DEVIATION HAND SPLINT

[76] Inventor: Julie Belkin, 806 Brantford Ave., Silver Spring, Md. 20904

[21] Appl. No.: 933,504

[22] Filed: Sep. 18, 1997

[51] Int. Cl.$^6$ ........................................................ A61F 5/00
[52] U.S. Cl. ............................................... 602/21; 602/16
[58] Field of Search ........................... 602/5, 16, 20–22; 128/878, 879; 601/40; 482/44–48

[56] References Cited

U.S. PATENT DOCUMENTS

| | | |
|---|---|---|
| 818,332 | 4/1906 | Anson . |
| 897,471 | 9/1908 | Loyola . |
| 4,456,002 | 6/1984 | Barber et al. . |
| 4,558,694 | 12/1985 | Barber . |
| 4,585,228 | 4/1986 | Olson . |
| 5,358,471 | 10/1994 | Klotz ........................................ 602/21 |
| 5,364,323 | 11/1994 | Liu .............................................. 482/45 |
| 5,372,145 | 12/1994 | Berger .................................... 602/20 X |
| 5,466,192 | 11/1995 | Castolo et al. ........................ 602/16 X |

Primary Examiner—Linda C.M. Dvorak
Attorney, Agent, or Firm—Weintraub & Brady

[57] ABSTRACT

A polycentric hinged ulnar deviation splint for reducing deviation of the fingers in an ulnarward direction and for bringing the fingers into neutral alignment along a mid-longitudinal axis of the hand and forearm which allows free joint motion in all fingers and has no covering of the palm of the hand is disclosed. The splint has a proximal portion and a distal portion which are opposed and conform to the dorsum of the hand. Each extension of the proximal portion and the distal portion are attached by a polycentric hinge which forms a multi-axis polycentric joint in alignment with the metacarpophalangeal joints of the hand. The splint also includes at least one finger alignment component which is attached to the distal portion, as well as a strap for removably fastening the splint on the hand.

10 Claims, 3 Drawing Sheets

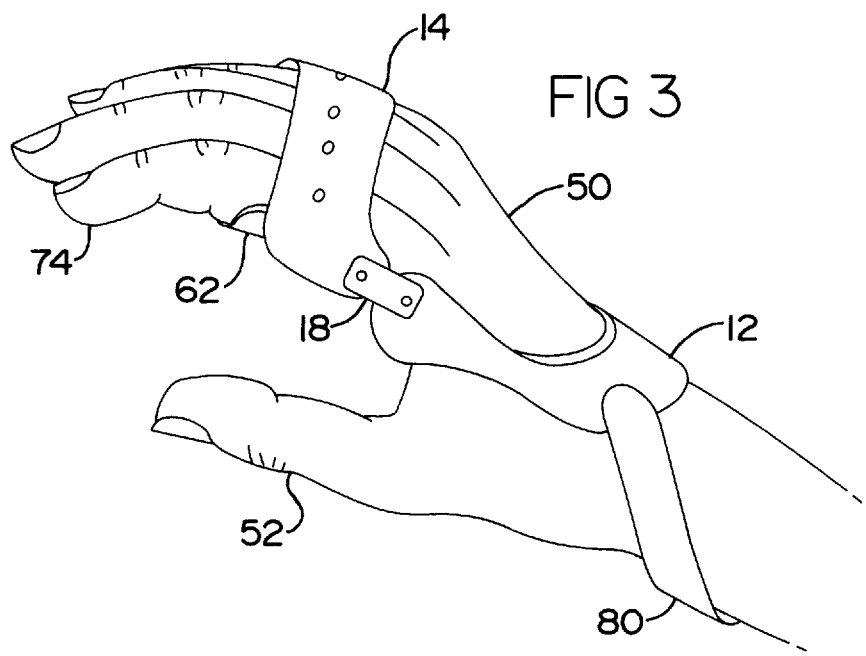
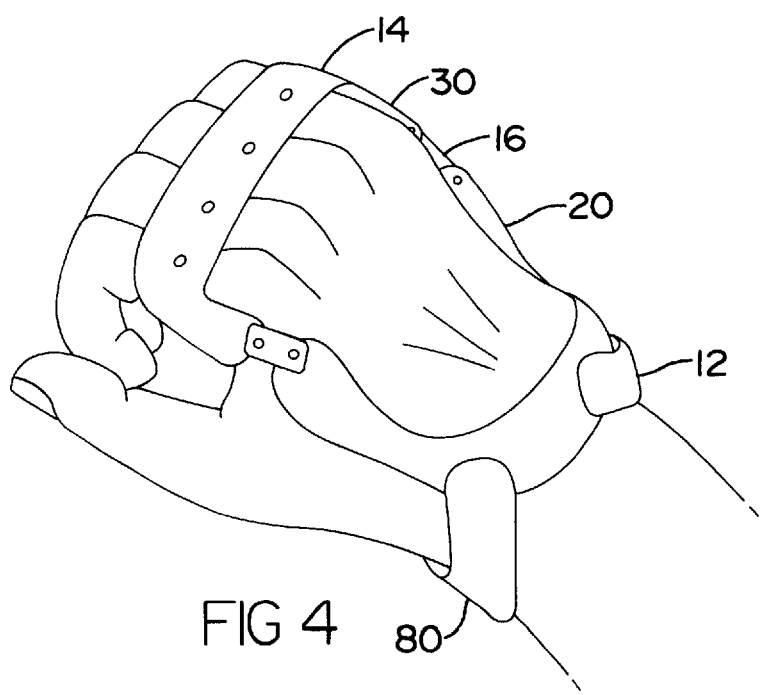

POLYCENTRIC HINGED ULNAR DEVIATION HAND SPLINT

BACKGROUND OF THE INVENTION

1. Field of the Invention

The present invention relates to hand splints. More particularly, the present invention relates to a hand splint which reduces deviation of the finger(s) in an ulnarward direction and brings the fingers into neutral alignment along a mid-longitudinal axis of the hand and forearm. Even more particularly, the present invention relates to a hand splint for supporting the metacarpophalangeal (MP) joints and for realigning the proximal phalanges when indicated by uncontrolled ulnar drift.

2. Description of Prior Art

The present invention is intended to be used by persons who experience uncontrolled deviation of the fingers in an ulnarward direction secondary to joint disruption caused by disease, such as Rheumatoid arthritis, or trauma affecting the hand. Persons with uncontrolled ulnar deviation experience diminished or lost hand function due to the inability to stabilize the fingers at the MP joints which is necessary to form and maintain a fisted posture or to achieve pinch between the thumb and finger(s).

Use of the impaired hand without any external support will cause progression of the instability at the MP joints as proportionally more pressure must be exerted to sustain objects in the hand or fingers. The required pressure furthers the stretching and destruction of the soft tissues at the joints and eventually renders them incapable of maintaining stability around the joint.

The loss of functional use of the hand for all but simple non-resistive tasks leads to a loss of independence for the affected person. Persons experiencing severe forms of arthritis frequently require assistance with daily tasks such as dressing, feeding and hygiene activities. Such persons may also be incapable of performing vocational activities due to the loss of hand function.

To alleviate this disruptive condition, there has been proposed, heretofore, splints and similar devices to assist such persons and to impact some function to the hand of the user. Such devices of this nature have been available for over ten years. All such prior art splint devices generally fall into two basic categories. The first category involves those splint devices which are comprised of flexible woven materials sewn into patterns that seek to support the fingers and hand, or more commonly, the fingers, hand and wrist. The flexible material splints frequently include flexible or rigid stays positioned to limit joint motion so as to offer support through immobilization of the joints. These splints are held in place on the hand or arm by the use of straps that incorporate a hooked area and an interlocking brushed material. The straps are positioned on the device to allow for independent donning and doffing of the device. Persons with arthritis frequently do not have sufficient strength to pull open these straps or to apply sufficient force on the strap for secure closure of the device on the hand and arm and therefore require the assistance of a care giver to don and doff the device. If this category of device is not positioned securely on the hand with firmly applied strapping, it may be displaced during activities rendering it an impediment to function rather than an assist.

The second category includes splint devices made from metal, plastic or wire formed to cover the palmar surface of the hand and include some form of semi-rigid or flexible pieces formed to position the fingers out of deviation. These splints have the advantage of being lightweight and of providing adjustability through the use of malleable fingers extensions or through the use of elastic components.

However, the second category of splint devices, as well as the first, suffer a disadvantage in that they cover the palmar surface of the hand with a bulky foam and metal frame rendering it more difficult to carry or manipulate objects. These devices also limit the ability of the wearer to close their hand into a fist because the devices do not allow motion in a plane of flexion towards the palm and extension away from the palm at the MP joints.

A further disadvantage of the prior art devices is that they are static in design. Designs which are static in nature allow no motion at the MP joints and, therefore, limit hand function as the hand must perform tasks without active flexion or extension.

In addition, the prior art devices as described are made from either flexible woven materials or from lightweight wire covered by a water resistant cushioning. These materials, while soft and providing cushioning around the involved fingers and hand, do not withstand repeated or aggressive activities and, therefore, require regular replacement which is costly and inconvenient.

It is therefore the goal of the present invention to overcome the problems heretofore encountered in the prior art. It is a purpose of the present invention to provide a hand splint which by placing the body of the splint on the dorsum of the hand leaves the palmar surface of the hand free of any encumbrance and allows for unimpeded functional grasp and release.

Furthermore, it is a purpose of the present invention to provide a hand splint which is hinged to allow for improved hand function in active flexion and extension.

In addition, the present invention allows for positioning and correction of each finger individually by the use of a finger alignment component that can be readily contoured to meet the shape and position of each finger. The present invention allows for free motion in a plane of flexion towards the palm and extension away from the palm at all joints of the hand.

It is a further purpose of the present invention to provide a hand splint that successfully maintains the fingers of the hand in a neutral alignment as measured from a longitudinal line bisecting the forearm and the hand and that also allows for fill functional use of the hand.

It is a still further purpose of the present invention to provide a hand splint made from materials which withstand repeated or aggressive activities so as to improve convenience and cost-effectiveness.

The present invention is designed to restore stability to the joints of the hand and thereby restore hand function and greater independence in all tasks.

SUMMARY OF THE INVENTION

In accordance with the present invention there is provided a polycentric hinged ulnar deviation splint comprising:

(a) a substantially "U"-shaped proximal portion having a pair of spaced-apart proximal extensions;

(b) a substantially "U"-shaped distal portion having a pair of spaced-apart distal extensions, (c) the proximal portion and the distal portion being in opposition to each other and conforming to the dorsum of a hand of a user, one proximal extension being associated with one distal extension;

(d) means for hingedly attaching an associated proximal extension to an associated distal extension;

(e) at least one finger alignment component attached to the distal portion; and (f) means for removably fastening the splint on the hand of the user.

The splint hereby reduces deviation of the fingers in an ulnarward direction and brings the fingers into neutral alignment along a mid-longitudinal axis of the hand and forearm allowing free joint motion without covering the palm of the hand.

The splint comprises a proximal portion and a distal portion which conform to the dorsum of the hand, thereby leaving the palmar surface of the hand free of any encumbrance and allows for unimpeded functional grasp and release.

The proximal portion and the distal portion are hingedly attached at an associated proximal extension and an associated distal extension, preferably through the use of a polycentric hinge. The use of the polycentric hinge lengthens the area around which the axis of rotation may occur. A single axis hinge must be in exact alignment with the axis of a joint for free motion to occur. The lengthened polycentric hinge provides free motion at the MP without the need to maintain exact alignment with the axis of the joint. The advantage of the polycentric hinge is seen in the absence of displacement of the splint on the hand during MP joint motion.

The splint of the present invention includes a finger alignment component which can be readily contoured to meet the shape and position of each finger to allow for the positioning and correction of each finger individually. The present invention allows for free motion in a plane of flexion towards the palm and extension away from the palm at all joints of the hand while maintaining the fingers of the hand in neutral alignment with a longitudinal line bisecting the forearm and the hand. This splint results in improved pinch and grip function for the user when this function is imperiled by uncontrollable ulnar drift at the MP joints.

The splint of the present invention is, preferably, fabricated from thermoplastic, aluminum or stainless steel which is a durable material that can withstand repeated and aggressive activities. The finger alignment component is, preferably, made from malleable aluminum segments covered in a heat processed plastic covering such as a sleeve or coating. The hand splint is, preferably, secured to the hand and wrist with a interlocking brushed strap which attaches to hook closures attached to the proximal portion of the splint.

The present invention will be more clearly understood with reference to the accompanying drawings, in which like reference numerals refer to like parts.

BRIEF DESCRIPTION OF THE DRAWINGS

FIG. 3 is a side view of the splint hereof in place on a hand with the fingers in an extended position;

FIG. 4 is a top view of the splint hereof in place on a hand with the fingers in a flexed position.

DESCRIPTION OF THE PREFERRED EMBODIMENT

Figure 1:
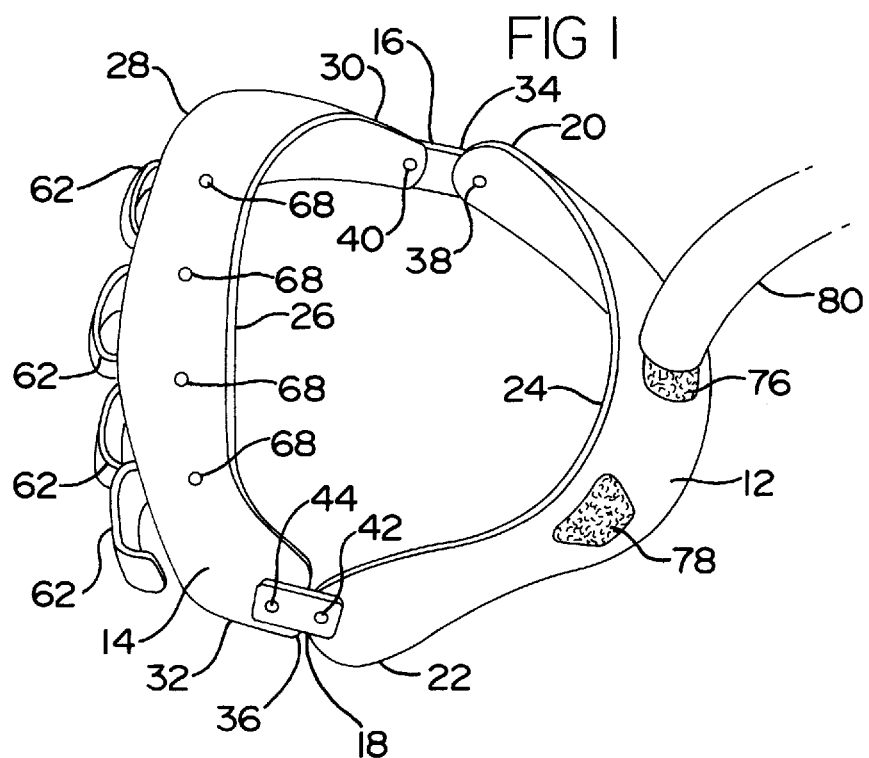
FIG. 1 is a perspective view of a splint according to the present invention.

As hereinabove noted, the present invention provides a polycentric hinged ulnar deviation splint comprising:

(a) a substantially "U"-shaped proximal portion having a pair of spaced-apart proximal extensions;

(b) a substantially "U"-shaped distal portion having a pair of spaced-apart distal extensions, (c) the proximal portion and the distal portion being in opposition and conforming to the dorsum of a hand of a user, one proximal extension being associated with one distal extension;

(d) means for hingedly attaching an associated proximal extension to an associated distal extension;

(e) at least one finger alignment component attached to the distal portion; and (f) means for removably fastening the splint on the hand of the user.

With reference now to FIGS. 1–5, there is shown therein, a splint 10 in accordance with the present invention for reducing deviation of the fingers in an ulnarward direction and for bringing and holding the proximal phalanges into alignment with a line drawn longitudinally bisecting the forearm and hand.

The splint 10 comprises a substantially "U"-shaped proximal portion 12 shaped to the dorsum of the hand 50 of the user having a lateral proximal extension 20, a medial proximal extension 22, and an interconnecting bight portion 24. The proximal portion 12 is configured to extend medially from the proximal edge of the fifth MP joint, curve over the dorsum of the hand 50 following the line of the dorsal wrist crease, and curve back along the lateral border of the second metacarpal bone to the proximal edge of the second MP joint. The proximal portion 12 is contoured to circumvent the area of the first dorsal interroseous muscle on the dorsum of the hand 50 to allow the thumb 52 free range of motion. The lateral proximal extension 20 lies in a plane parallel to the fifth MP joint and the medial proximal extension 22 lies in a plane parallel to the second MP joint.

The splint 10 also comprises a substantially "U"-shaped distal portion 14 shaped to the dorsal arch of the proximal phalanges. The distal portion 14 has a first edge 26, a second edge 28, a medial distal extension 30, and a lateral distal extension 32. The first edge 26 and the second edge 28 extend from the distal edge of the MP joints to the proximal edge of the proximal interphalangeal (PIP) joints. The lateral distal extension 30 is configured to extend distally to the distal edge of the fifth MP joint and lies in a plane parallel to the fifth MP joint. The medial distal extention 32 is configured to extend distally to the distal edge of the second MP joint and lies in a plane parallel to the second MP joint.

Figure 2:
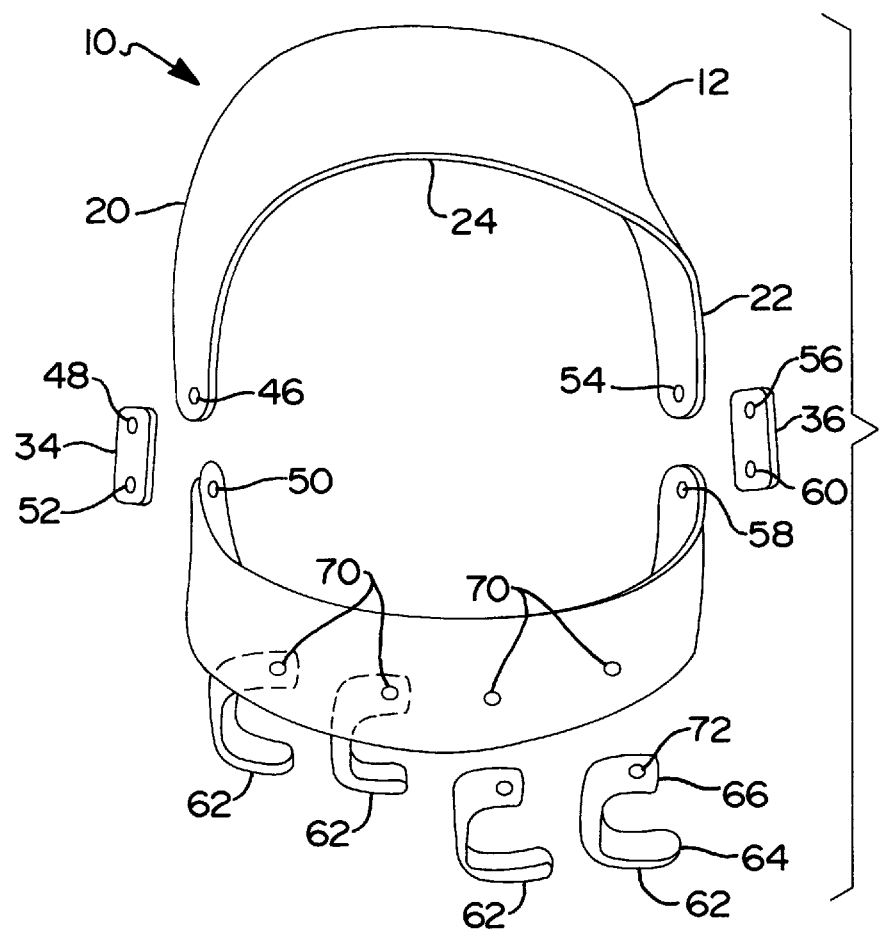
FIG. 2 is an exploded perspective view of the splint hereof.

The splint 10 hereof includes means for hingedly attaching the lateral proximal extension 20 to the lateral distal extension 30. The means for hingedly attaching is, preferably, a lateral polycentric hinge 16 comprising a lateral polycentric hinge plate 34 and at least two lateral rivets 38 and 40. Similarly, the means for hingedly attaching the medial proximal extension 22 to the medial distal extension 32 is, preferably a medial polycentric hinge 18 comprising a lateral polycentric hinge plate 36 and at least two medial rivets 42 and 44. The medial polycentric hinge 16 and the medial polycentric hinge 18 are alike. The lateral polycentric hinge plate 34 is hingedly attached to lateral proximal extension 20 and lateral distal extension 30 by lateral rivets 38 and 40 which project through suitable openings 46, 48, 51 and 52 as shown in FIG. 2. Likewise, the medial polycentric hinge plate 36 is hingedly attached to medial proximal extension 22 and medial distal extension 32 by medial rivets 42 and 44 which project through suitable openings 54, 56, 58 and 60 as shown in FIG. 2. The medial polycentric hinge 16 and the lateral polycentric hinge 18 each form a multi-axis polycentric joint in alignment with the MP joints of the hand.

It is to be appreciated that the medial proximal extension 20 and the medial proximal extension 22 are a pair of spaced apart proximal extensions. Likewise, the lateral distal extension 30 and the medial distal extension 32 are a pair of spaced apart distal extensions.

Furthermore, it is to be appreciated that the lateral proximal extension 20 and the lateral distal extension 30 may be defined as an associated proximal extension and and associated distal extension. Likewise, the medial proximal extension 22 and the medial distal extension 32 may be defined as an associated proximal extension and and associated distal extension.

It is to be further appreciated that the lateral polycentric hinge 16 and the medial polycentric hinge 18 may be defined as at least one polycentric hinge. Accordingly, the proximal portion 12 and the distal portion 14 are in opposition and conform to the dorsum of the hand. The proximal extensions and the distal extensions are, likewise, in opposition, and an associated proximal extension and an associated distal extension are hingedly attached by at least one polycentric hinge.

FIG. 2 provides an exploded view in the sagittal plane of the present invention and, in particular, of a finger alignment component 62. The component 62 is an arcuate member having a first end 64 and a second end 66. The first end 64 of the component 62 is rounded to afford a smooth edge that will not impinge into the space between the fingers. The second end 66 of the component 62 is attached to distal portion 14 by a distal rivet 68 which projects through suitable openings 70 and 72. The component 62 is rotatable at the point of the distal rivet 68 to assist in aligning the splint 10 to the finger 74. The suitable openings 70 and 72 are placed so that the component 62 is readily positionable to support and/or correct a finger of a user.

As seen in FIG. 1, a lateral hook closure 76 and a medial hook closure 78 are fixedly attached at the proximal end of proximal portion 12. An interlocking brushed strap 80 is removably attached to the lateral hook closure 76 and the medial hook closure 78. The interlocking brushed strap 80 defines a means for removably mounting or removably fastening the splint on the hand of a user. To act as a restraint to the displacement of splint 10, the interlocking brush strap 80 is attached to either the lateral hook closure 76 or the medial hook closure 78 and is wrapped under the dorsum of the wrist at the level of the wrist crease and is attached back onto the unutilized hook closure 76 or 78.

FIGS. 3 and 4 readily illustrate the use of the present invention. FIG. 3 illustrates that the fingers can be extended while maintaining neutral alignment with the long axis of the hand and forearm with the splint 10 in place on the dorsum of the hand 50. FIG. 4 illustrates that the fingers can be flexed while maintaining neutral alignment with the long axis of the hand and forearm with the splint 10 in place on the dorsum of the hand 50.

Figure 5:
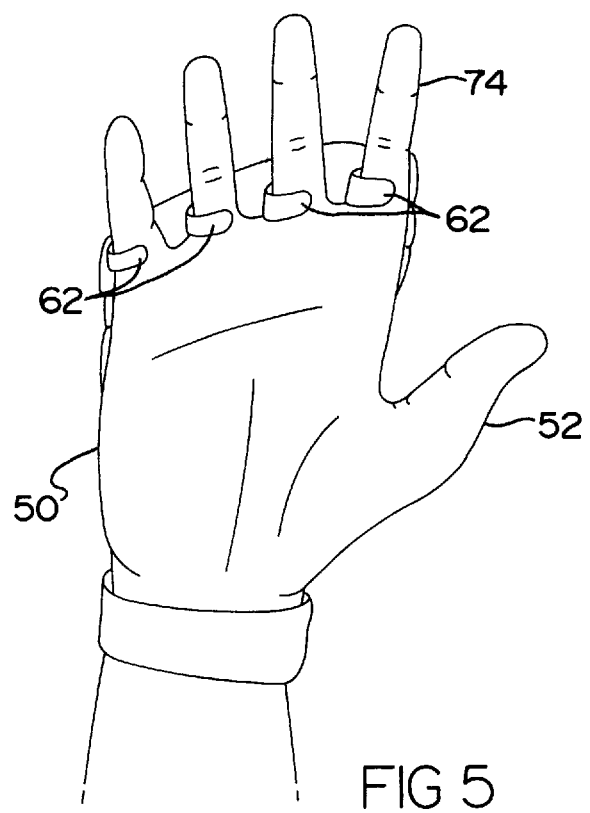
FIG. 5 is a bottom view of the splint hereof in place on a hand with the fingers in an extended position.

FIG. 5 readily illustrates the further advantages of the invention. In a palmar view, only the finger alignment component 62 is seen to cover the palmar surface of the hand.

In a preferred embodiment, the proximal portion 12, the distal portion 14, the lateral polycentric hinge 16 and the medial polycentric hinge 18 are fabricated from a heat moldable high temperature thermoplastic, aluminum or stainless steel. The distal rivet 68, the lateral rivets 38 and 40 and the medial rivets 42 and 44 are, preferably, two-part compressed aluminum rivets or stainless steel speedy style rivets. The finger alignment component is, preferably, fabricated from malleable aluminum into segments and covered in a heat processed plastic covering such as a sleeve or coating. The heat processed plastic covering provides a non-abrasive cushioned covering for a finger alignment component which is comfortable and durable. The edges of the heat processed plastic covering are rounded to distribute pressure and to provide comfort to the user. The heat processed plastic covering is rated to have a usable life of five years or greater before replacement may be necessary.

The invention leaves the palmar surface of the hand free of any encumbrances and allows for unimpeded functional grasp and release by fitting the body of the splint on the dorsal surface of the hand and having polycentric hinges at both the second and the fifth MP joints. Only the finger alignment components cover the palmar surface of the hand and act functionally as restraining finger rings. The polycentric hinge allows for two sites of movement around which MP joint flexion and extension can occur thereby lessening the potential for migration of the body of the splint on the hand. Free movement of the MP joints and the lack of any palmar covering in the hand also allows free flexion and extension at the PIP and distal interphalangeal (DIP) joints so that full grasp and release is possible.

Although the present invention has been described herein with respect to a specific embodiment thereof, it will be understood that the foregoing description is intended to be illustrative, and not restrictive. Many modifications of the present invention will occur to those skilled in the art to which the present invention is directed. All such modifications which fall within the scope of the claims hereinbelow are intended to be within the scope and spirit of the present invention.

Having, thus, claimed the invention, what is claimed is:

1. A polycentric hinged ulnar deviation splint comprising:
   (a) a substantially "U"-shaped proximal portion having a pair of spaced-apart proximal extensions,
   (b) a substantially "U"-shaped distal portion having a pair of spaced-apart distal extensions;
   (c) the proximal portion and the distal portion being in opposition and being sized and configured to conform to the dorsum of a hand of a user, one proximal extension being associated with one distal extension,
   (d) at least one polycentric hinge for hingedly attaching an associated proximal extension to an associated distal extension;
   (e) at least one finger alignment component attached to the distal portion; and
   (f) means for removably fastening the splint on a hand of a user.

2. The splint of claim 1, wherein the proximal portion is contoured to circumvent the area of the first dorsal interosseous muscle to allow a thumb of a user free range of motion.

3. The splint of claim 1, wherein the polycentric hinge comprises a polycentric hinge plate and at least two rivets.

4. The splint of claim 3, wherein the polycentric hinge plate is of a material selected from the group consisting of thermoplastic, aluminum and stainless steel.

5. The splint of claim 1, wherein the at least one finger alignment component comprises an arcuate member.

6. The splint of claim 4, wherein the at least one finger alignment component is a malleable aluminum segment.

7. The splint of claim 5, wherein the at least one finger alignment component further comprises a heat processed plastic covering.

8. The splint of claim 1, wherein the fastening mean for holding the splint of the hand comprises an interlocking brush strap having a first end and a second end, a medial hook closure, and a lateral hook closure, the strap being removably attached at the first end to the medial hook closure and at the second end to the lateral hook closure.

9. The splint of claim 7, wherein the interlocking brush strap further comprises a cushion.

10. The splint of claim 1, wherein the proximal portion and the distal portion are of a material selected from the group consisting of thermoplastic, aluminum and stainless steel.

* * * * *